United States Patent [19]

Umumura et al.

[11] 4,401,830
[45] Aug. 30, 1983

[54] PROCESS FOR PREPARATION OF 3-ALKOXY-4-HYDROXYPHENYLACETIC ACID

[75] Inventors: Sumio Umumura; Fumio Iwata; Kikuo Ataka; Hiroshi Shiraishi, all of Ube, Japan

[73] Assignee: UBE Industries, Ltd., Ube, Japan

[21] Appl. No.: 222,155

[22] Filed: Jan. 2, 1981

[30] Foreign Application Priority Data

Jan. 11, 1980 [JP] Japan ................................. 55-1358

[51] Int. Cl.$^3$ .............................................. C07C 65/01
[52] U.S. Cl. .................................... 562/478; 562/470
[58] Field of Search ........................................ 562/478

[56] References Cited

U.S. PATENT DOCUMENTS 4,198,526 4/1980 Edwards .............................. 562/478

FOREIGN PATENT DOCUMENTS 2445311 12/1978 France ................................. 562/478
53-92344 12/1978 Japan ................................... 562/478

Primary Examiner—Paul J. Killos
Attorney, Agent, or Firm—Frishauf, Holtz, Goodman & Woodward

[57] ABSTRACT

3-Alkoxy-4-hydroxyphenylacetic acid useful as intermediate for preparation of pharmaceuticals is prepared by catalytic reduction with hydrogen using a palladium catalyst of corresponding 3-alkoxy-4-hydroxymandelic acid occurring as the reaction product between 2-alkoxyphenol and glyoxylic acid at high conversion and yield.

10 Claims, No Drawings

PROCESS FOR PREPARATION OF 3-ALKOXY-4-HYDROXYPHENYLACETIC ACID

This invention relates to a process for preparing 3-alkoxy-4-hydroxyphenylacetic acid by catalytic reduction of corresponding 3-alkoxy-4-hydroxymandelic acid with hydrogen using a palladium catalyst. More particularly, the present invention relates to a process for preparing 3-alkoxy-4-hydroxyphenylacetic acid directly from a reaction mixture containing 3-alkoxy-4-hydroxymandelic acid prepared by the addition reaction between 2-alkoxyphenol and glyoxylic acid in the presence of an alkali.

As is well known in the art, 4-hydroxyphenylacetic acid or its derivatives are useful intermediates for preparation of pharmaceuticals. For example, U.S. Pat. No. 2,487,019 discloses a process for producing an antibiotic p-hydroxybenzylpenicillin sodium by adding a 4-hydroxyphenylacetic acid into a culture medium for production of penicillins. British Pat. No. 1,285,038 discloses a process for producing athenorol to be administered as β-blocking agent by converting 4-hydroxyphenylacetic acids to 1-p-carbamoylmethylphenoxy-2,3-epoxypropane, which is in turn allowed to react with isopropyl amine. Further, German laid-open patent application No. 2,621,090 discloses preparation of 2-(p-hydroxyphenyl)-3-amino-1-propanol derivatives having bronchiectatic activity from 4-hydroxyphenylacetic acids.

As a method for preparation of 4-hydroxyphenylacetic acids known in the art, Japanese Provisional Patent Publication No. 76542/1979 discloses a process, comprising reducing 3-chloro-4-hydroxymandelic acid using red phosphorus, tin or stannous chloride. According to this method, however, it is required to use a stoichiometric amount of a reducing agent and hence considerable difficulties in operation are encountered in commercial application. Belgian Pat. No. 867,289 discloses a process, comprising reducing sodium 4-hydroxymandelate with hydrogn in water in the presence of a palladium catalyst and chloride anion. According to this process, however, a large quantity of chloride compounds such as hydrochloric acid, sodium chloride, potassium chloride, etc. are required to be added in order to maintain a high yield of the desired products. For this reason, it is necessary to be careful about corrosion of the apparatus as well as handling of chloride compounds. Another difficulty resides in the isolation step required for separation of the starting compounds, i.e. 4-hydroxymandelic acids, generally in the form of pure crystals from the reaction mixture resulting from the preparation of said starting compounds. Thus, it would be desirable to prepare 4-hydroxyphenylacetic acid directly from a reaction mixture containing a 4-hydroxymandelic acid as the reaction product.

According to the present invention, there is provided a process for preparing a 3-alkoxy-4-hydroxyphenylacetic acid, which comprises allowing a 2-alkoxyphenol to react with glyoxylic acid in the presence of an alkaki to obtain 3-alkoxy-4-hydroxymandelic acid, and then subjecting the resulting reaction mixture containing said 3-alkoxy-4-hydroxymandelic acid as such to catalytic reduction with hydrogen using a palladium catalyst while controlling the pH value of said reaction mixture at not higher than 4.

As the 3-alkoxy-4-hydroxymandelic acid to be used in the present invention, there may be mentioned 3-methoxy-4-hydroxymandelic acid, 3-ethoxy-4-hydroxymandelic acid, 3-propoxy-4-hydroxymandelic acid, 3-butoxy-4-hydroxymandelic acid and the like. These 3-alkoxy-4-hydroxymandelic acids can readily be prepared by, for example, the addition reaction between the 2-alkoxyphenols and glyoxylic acid in the presence of an alkali. In the present invention, said addition reaction mixture containing such 3-alkoxy-4-hydroxymandelic acid is provided for use as such without any step for isolation of 3-alkoxy-4-hydroxymandelic acid.

The addition reaction may be carried out by heating a mixture of 2-alkoxyphenol and glyoxylic acid in the copresence of an alkali under stirring. The composition of the starting mixture may generally be such that 2-alkoxyphenol is equimolar to or slightly in excess over glyoxylic acid. There is no limitation of the method for charging the starting materials. According to one method, for example, an alkaline aqueous solution may be added to a mixture of 2-alkoxyphenol and an aqueous glyoxylic acid solution. The reaction may be carried out at a temperature in the range from 0° to 40° C. The reaction time, which may vary depending on the reaction temperature, is in the range from 6 to 24 hours.

The composition of the thus prepared addition reaction mixture comprises 82 to 86% by weight of 3-alkoxy-4-hydroxymandelic acid, 4 to 5% by weight of 3-alkoxy-2-hydroxymandelic acid and 9 to 14% by weight of 3-alkoxy-2-hydroxy-5-(hydroxycarboxymethyl)-mandelic acid based on the total products of the addition reaction.

The palladium catalyst to be employed in the process of the present invention may suitably be one, comprising metallic palladium supported on a carrier such as activated charcoal, graphite, silica gel, barium sulfate, calcium carbonate or alumina, in an amount of 0.1 to 10% by weight, preferably 0.5 to 8% by weight. Such a palladium catalyst may be prepared by dissolving palladium chloride in conc. hydrochloric acid, followed by impregnation onto a carrier, and thereafter optionally treating the carried product with a reducing agent such as hydrogen with subsequent removal of the residual hydrochloric acid. The palladium catalyst is to be employed in an amount of 0.001 to 2.0 g, preferably 0.01 to 0.5 g, as calculated on the basis of metallic palladium, per mole of 3-alkoxy-4-hydroxymandelic acid.

According to the present invention, it is essentially required to control the pH value of the addition reaction mixture at not higher than 4, preferably in the range from 1 to 2, in carrying out the hydrogen reduction reaction using the resultant mixture from the addition reaction between 2-alkoxyphenol and glyoxylic acid in the presence of an alkali as described above. Such a pH control can be effected by conventional methods by, for example, adding an acid such as sulfuric acid or hydrochloric acid, or acetic acid. Under these conditions, neither 3-alkoxy-2-hydroxymandelic acid nor 3-alkoxy-2-hydroxy-5-(hydroxycarboxymethyl)-mandelic acid is found to be substantially reactive.

As the hydrogen, there may be employed pure hydrogen or a hydrogen containing gas comprising a mixture of hydrogen with an inert gas such as nitrogen or argon. The pressure of hydrogen may be in the range from 0.1 to 15 Kg/cm$^2$ (gauge), preferably from 3 to 8 Kg/cm$^2$(gauge). The reaction may be carried out at a temperature from 0° to 200° C., preferably, at around 100° C.

The desired product obtained according to the process of the present invention is a 3-alkoxy-4-hydroxyphenylacetic acid corresponding to the starting 3-alkoxy-4-hydroxymandelic acid.

The reaction mixture obtained according to the process of the present invention may be generally cooled and subjected to filtration to remove insolubles such as the catalyst. Isolation of 3-alkoxy-4-hydroxyphenylacetic acid from the filtrate may be conducted by the following methods. One method comprises concentrating or cooling to lower than the room temperature the filtrate to thereby precipitate 3-alkoxy-4-hydroxyphenylacetic acid, followed by collection by filtration. According to another method, the filtrate is extracted with a solvent such as an acetic acid ester, an ether or an aromatic hydrocarbon, followed by evaporation of the solvent, to give the desired product, namely 3-alkoxy-4-hydroxyphenylacetic acid.

By practicing the process of the present invention, it is possible to produce a 3-alkoxy-4-hydroxyphenylacetic acid from corresponding 3-alkoxy-4-hydroxymandelic acid at a high conversion as well as at a high yield.

Conversions of 3-alkoxy-4-hydroxymandelic acid and yields of 3-alkoxy-4-hydroxyphenylacetic acid as shown in the following Examples and Comparative examples were calculated by the formulas shown below:

$$\text{Conversion (\%)} = \frac{\text{3-alkoxy-4-hydroxymandelic acid reacted(mole)}}{\text{3-alkoxy-4-hydroxymandelic acid charged(mole)}} \times 100$$

$$\text{Yield (\%)} = \frac{\text{3-alkoxy-4-hydroxyphenylacetic acid formed(mole)}}{\text{3-alkoxy-4-hydroxymandelic acid charged(mole)}} \times 100$$

EXAMPLE 1

Into a mixture of 48 g of 40% aqueous glyoxylic acid and 34 g of 2-methoxyphenol, there was added 220 g of 9 wt.% aqueous sodium hydroxide. Then, the reaction was carried out at about 10° C. for 20 hours under stirring.

The thus prepared addition reaction mixture (0.3 liter), containing 39 g of 3-methoxy-4-hydroxymandelic acid, 2 g of 3-methoxy-2-hydroxymandelic acid and 7 g of 3-methoxy-2-hydroxy-5-(hydroxycarboxymethyl)-mandelic acid was adjusted to pH 1.5 by adding 20 N sulfuric acid thereto and then charged into an autoclave together with 0.4 g of 5 wt.% palladium-activated charcoal. While maintaining the hydrogen pressure at 5 Kg/cm²(gauge), the reaction was carried out at 80° C. under stirring for 12 hours. As the result, conversion of 4-hydroxy-3-methoxymandelic acid was found to be 92% and yield of 4-hydroxy-3-methoxyphenylacetic acid 77%.

EXAMPLE 2

The reaction was carried out in the same manner as in Example 1 except that acetic acid was used in place of 20 N sulfuric acid for adjustment to pH 1.5. As the result, conversion of 4-hydroxy-3-methoxymandelic acid was found to be 75% and yield of 4-hydroxy-3-methoxyphenylacetic acid 62%.

EXAMPLE 3

The reaction was carried out, using the addition reaction mixture containing 3-ethoxy-4-hydroxymandelic acid, which had been prepared by the reaction similarly as in Example 1 between 2-ethoxyphenol and glyoxylic acid in the presence of an alkali, under otherwise the same conditions as in Example 1. As the result, conversion of 3-ethoxy-4-hydroxymandelic acid was found to be 87% and yield of 3-ethoxy-4-hydroxyphenylacetic acid 71%.

COMPARATIVE EXAMPLE 1

Example 1 was repeated except that the pH of the reaction mixture was adjusted to 5, whereby the results obtained were found to be 35% of the conversion and 30% of the yield.

We claim:
1. A process for preparing a 3-alkoxy-4-hydroxyphenylacetic acid, which comprises reacting a 2-alkoxyphenol with glyoxylic acid in the presence of an alkali to form a reaction mixture containing 3-alkoxy-4-hydroxymandelic acid together with 3-alkoxy-2-hydroxymandelic acid, and 3-alkoxy-2-hydroxy-5(hydroxycarboxymethyl)-mandelic acid, and then subjecting said reaction mixture containing said 3-alkoxy-4-hydroxymandelic acid to catalytic redution with hydrogen using a palladium catalyst while controlling the pH value of said reaction mixture at not higher than 4 to form said 3-alkoxy-4-hydroxyphenylacetic acid without substantially reducing said 3-alkoxy-2-hydroxymandelic acid and said 3-alkoxy-2-hydroxy-5(hydroxycarboxymethyl-mandelic acid and then separating said 3-alkoxy-4-hydroxyphenylacetic acid from said reaction mixture.

2. The process as in claim 1, wherein the pH value is controlled at from 1 to 2.

3. The process as in claim 1 or 2, wherein the catalytic reduction is carried out under a hydrogen pressure of 0.1 to 15 Kg/cm².

4. The process as in claim 1 or 2, wherein the palladium catalyst is supported on a carrier.

5. The process as in claim 1 or 2, wherein the catalytic reduction is carried out at a temperature from 0° to 200° C.

6. The Process as in claim 3, wherein the palladium catalyst is supported on a carrier.

7. The process as in claim 3, wherein the catalytic reduction is carried out at a temperature from 0° to 200° C.

8. The process as in claim 4, wherein the catalytic reduction is carried out at a temperature from 0° to 200° C.

9. The process as claimed in claim 1 or 2, wherein said alkoxy is selected from the group consisting of methoxy, ethoxy, propoxy, and butoxy.

10. The process as claimed in claim 7, wherein said alkoxy is selected from the group consisting of methoxy, ethoxy, propoxy, and butoxy.

* * * * *